(12) United States Patent
Ouzounian

(10) Patent No.: US 9,087,300 B2
(45) Date of Patent: *Jul. 21, 2015

(54) METHOD TO PREDICT HOMEMADE EXPLOSIVE FORMULATION OUTCOMES

(76) Inventor: Gregory Albert Ouzounian, Castro Valley, CA (US)

( * ) Notice: Subject to any disclaimer, the term of this patent is extended or adjusted under 35 U.S.C. 154(b) by 545 days.

This patent is subject to a terminal disclaimer.

(21) Appl. No.: 13/507,402

(22) Filed: Jun. 25, 2012

(65) Prior Publication Data

US 2014/0304208 A1     Oct. 9, 2014

Related U.S. Application Data

(63) Continuation of application No. 12/455,345, filed on Jun. 1, 2009, now Pat. No. 8,224,764.

(51) Int. Cl.
| G06F 17/00 | (2006.01) |
| G06N 5/02 | (2006.01) |
| G06N 5/04 | (2006.01) |
| G06F 19/00 | (2011.01) |

(52) U.S. Cl.
CPC .............. G06N 5/046 (2013.01); G06F 19/704 (2013.01); G06F 19/705 (2013.01)

(58) Field of Classification Search
None
See application file for complete search history.

(56) References Cited

U.S. PATENT DOCUMENTS

| 5,950,192 A * | 9/1999 | Moore et al. ........................... 1/1 |
| 7,542,991 B2 * | 6/2009 | Ouzounian ............................ 1/1 |
| 2002/0169755 A1 * | 11/2002 | Framroze et al. ................. 707/3 |
| 2004/0093340 A1 * | 5/2004 | Edmondson et al. ......... 707/101 |
| 2004/0220753 A1 * | 11/2004 | Tabe ............................... 702/32 |
| 2009/0125460 A1 * | 5/2009 | Hewison et al. ................ 706/11 |

OTHER PUBLICATIONS

Combating Terrorism Technical Support Office 2008 Review.*
Homemade Explosives (HME) Program Overview—2008 Doug Bauer, PhD Explosives Division Science and Technology Directorate.*

* cited by examiner

*Primary Examiner* — Kakali Chaki
*Assistant Examiner* — Ababacar Seck
(74) *Attorney, Agent, or Firm* — Gregory Albert Ouzounian

(57) ABSTRACT

A method and an apparatus utilizing a digital computer programmed for the purpose to perform a virtual combination of potential source chemicals, found in a raid or a chemical cache, for the manufacture of Homemade Explosives (HMEs), so as to transform the raw inventory of found chemicals quickly and accurately into a readily understandable output predicting the various HME formulations whose manufacture was contemplated by a would-be bomb maker, along with an assessment of the relative likelihoods of each such possible HME outcome.

33 Claims, 6 Drawing Sheets

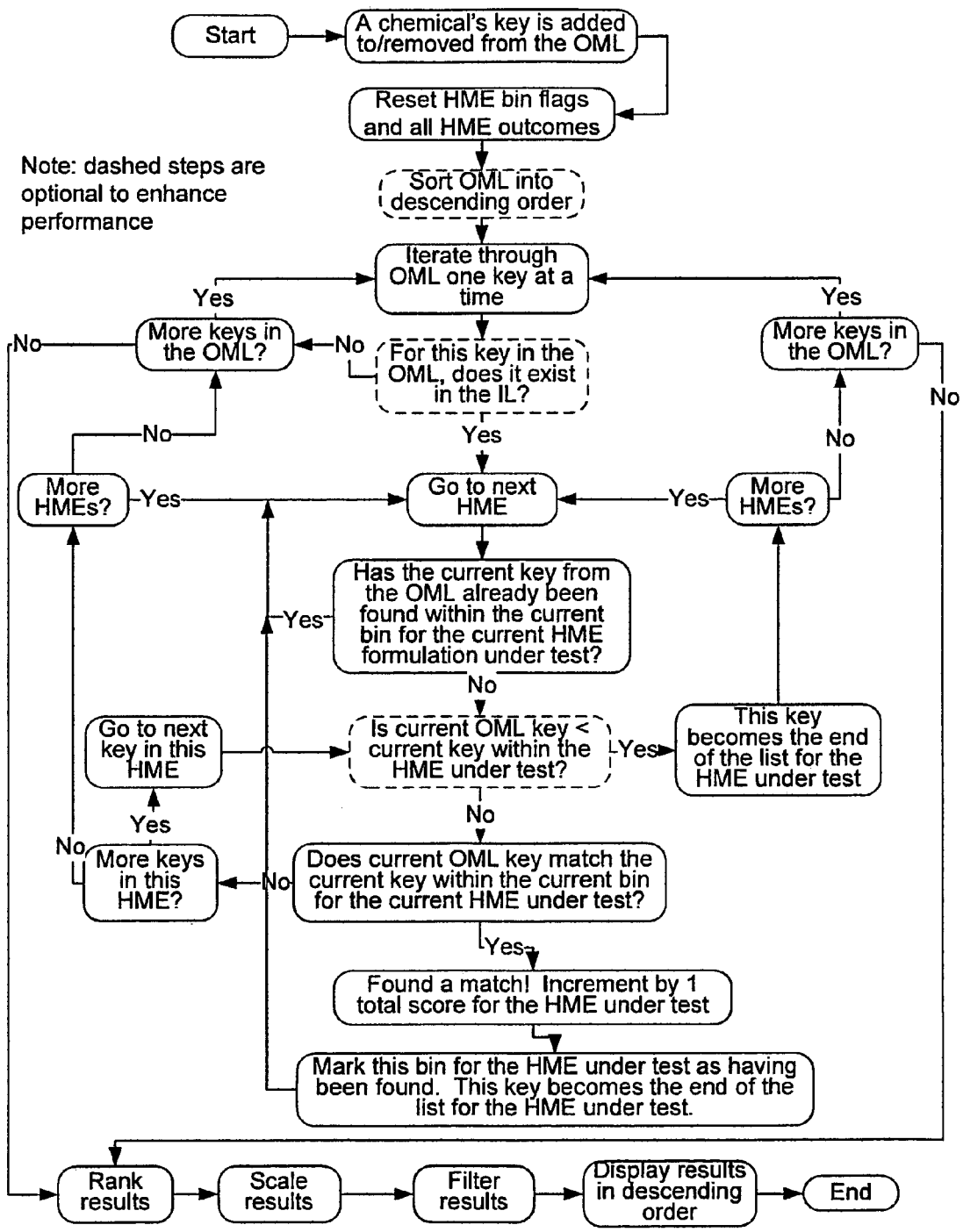

| | | | |
|---|---|---|---|
| APE | 418 | 1 | 0 |
| APE | 639 | 1 | 0 |
| APE | 1142 | 0 | 1 |
| APE | 1143 | 0 | 0 |
| APE | 2519 | 1 | 1 |
| APE | 2520 | 1 | 0 |
| APE | 4316 | 3 | 0 |
| APE | 4333 | 3 | 1 |
| APE | 4334 | 3 | 0 |
| APE | 4336 | 3 | 0 |
| APE | 4337 | 3 | 0 |
| APE | 4338 | 3 | 0 |
| APE | 4339 | 3 | 0 |
| APE | 4340 | 3 | 0 |
| APE | 4341 | 3 | 0 |
| APE | 4342 | 3 | 0 |
| APE | 4343 | 3 | 0 |
| APE | 4344 | 3 | 0 |
| APE | 4345 | 3 | 0 |
| APE | 4346 | 3 | 0 |
| APE | 4347 | 3 | 0 |
| APE | 4348 | 3 | 0 |
| APE | 4349 | 3 | 0 |
| APE | 4351 | 3 | 0 |
| APE | 5251 | 2 | 1 |
| APE | 5252 | 2 | 0 |
| APE | 5253 | 2 | 0 |
| APE | 5254 | 2 | 0 |
| APE | 5255 | 2 | 0 |

| List of user specificed chemicals internal keys |
|---|
| 5 |
| 4 |
| 3 |
| 2 |
| 1 |

| List of chemical internal keys for all chemicals part of an explosive formulation's key or alternate ingredients |
|---|
| 1 |
| 2 |
| 3 |
| 4 |
| 5 |
| 6 |
| 7 |
| 8 |
| 9 |
| 10 |

METHOD TO PREDICT HOMEMADE EXPLOSIVE FORMULATION OUTCOMES

Note: This application is a Continuation of application Ser. No. 12/455,345, by the same sole inventor, Gregory Albert Ouzounian, and claims priority from that application's filing date of Jun. 1, 2009. Examination was by Examiner Ababacar Seck, Art Unit 2129.

FIELD OF THE INVENTION

The invention relates to the field of law enforcement and anti-terrorism, more specifically to assessment of a threat from persons seeking to produce homemade explosives.

BACKGROUND OF THE INVENTION

Law enforcement, the military and other government agencies are commonly faced with the challenge of trying to identify which, if any, dangerous homemade explosives ("HMEs") someone may be trying to formulate from a given set of chemical ingredients, as for example those found at the scene of a crime, or a raid (the Observed Materials).

As there may be many potential precursor materials found, and there are many explosive formulations, each with multiple primary and secondary source materials, that a would-be bomb maker may be using, this task is both analytically difficult and extremely time consuming to accomplish, and virtually impossible to do at the scene of the raid or seizure, except in the case of the very simplest of explosive formulations, such as ammonium nitrate and fuel oil, which combine to form the binary explosive commonly referred to as ANFO. This problem has significantly hindered the responsible soldiers' or law enforcement officers' performance of their duties in this regard, for many years. Previous to this invention, making an assessment about what HMEs, if any, had been contemplated by the owners of a cache of chemicals required the person seeking such an assessment to send the inventory of materials to one of a small number of explosives experts at an agency like the FBI or BATF, where the expert would attempt to intuit, from his or her experience, what the would-be bomb makers were up to, in terms of intended end-product explosives. So far as applicant is aware, no even moderately comprehensive database of all known explosives precursors existed—the closest thing known to the applicant is a small 2-sided card handed out by the FBI, entitled "Improvised Explosives Threat Card," listing fewer than 20 commonly seen HME's and only their, typically two to four, primary preferred ingredients.

With the rise of terrorism and the Global War On Terror, U.S. and allied military forces, and other military and law enforcement organizations, and even emergency responders, have compelling operational reasons to be concerned about potential HME formulations. A typical scenario may involve a raid on a location or facility where the raiding forces come across a cache of chemicals. The ability to virtually combine these chemical components, on the spot, and thereby rapidly and accurately predict what were the most likely explosive formulations, if any, being manufactured (e.g., TNT, TATP, ANFO etc.), would provide valuable, timely, insight and situational awareness that is not currently available.

What is needed is a method and an apparatus for performing that virtual combination of discovered potential HME ingredients, so as to quickly and accurately predict the various explosive formulations whose manufacture was or may have been contemplated by the materials' users, along with an assessment of the relative likelihood of each such possible outcome, and to make that prediction and assessment immediately available to the user, in a readily understandable form. Preferably, it should be possible to perform the analysis and reach those conclusions right at the scene of the chemical cache under investigation.

SUMMARY OF THE INVENTION

This need, and others that will become apparent, are met by the current invention. A main object of the invention is to transform a raw list of materials found to be present in a chemical cache discovered in a raid or other investigation, into a comprehensive, detailed, easily understandable assessment of which homemade explosives formulations may have been the intended products of the persons in possession of the materials, and the relative likelihoods of those various HME formulations. Another object of this invention is to permit this assessment to be performed easily, at the scene of the raid or chemical cache under investigation if appropriate, by allowing the method to be carried out on a device sufficiently portable to be easily carried to the location, or even be carried at all times, by a user. Another object of this invention is to allow this assessment to be performed quickly, with results available in a matter of seconds after entry of the final observed material under evaluation. Another object of the invention is to permit the user to perform "what-if" tests on the chemical inventory found, by adding or deleting real or hypothetical chemicals to the list of observed materials, and immediately see the impact of such changes on the relative likelihoods of various HME formulations.

The invention utilizes a digital computer, comprising user input and output devices, memory, and processing devices, which is programmed to perform the following operations:

(1) storing a database (the "Chemicals Database") of chemicals, comprising known source chemicals from which specific HMEs can potentially be created, (2) storing a database (the "HME Database") comprising HMEs of interest and their formulations, i.e., the source chemicals from combinations of which each HME of interest can be made, (3) permitting a user to utilize a user input device (and the term "user input device" includes not only a keyboard, stylus, touchpad, or other device to manually enter the data, but also potentially a port permitting external devices such as chemical sensors that identify, by IR spectroscopy or other methods, the chemical species under investigation) to select from among the chemicals included in the Chemicals Database those chemicals actually present in a chemical cache of interest, or additional hypothetical chemicals as to which the user wishes to see how results would differ were they also present, and adding those selected chemicals to an Observed Materials List (OML), which is then stored in computer memory, (4) utilizing an algorithm created for the purpose to model probable HME formulation outcomes associated with the source chemicals found to be present, i.e., to determine what possible HMEs, if any, were intended to be produced from the reported source chemicals, by comparing the Observed Materials List to the HME Database, and calculating the relative likelihoods of each possible HME formulation, and, (5) utilizing a user output device to present the resulting relative likelihoods of each such possible HME formulation to the user in an easily understandable form.

These steps are carried out anew each time a new Observed Material is added to, or a previously selected material deleted from, the OML, to permit real-time "what-if" testing of real and hypothetical combinations of found chemicals.

It will be apparent that, with the addition of appropriate databases structured like the HME database, and the addition of source chemicals to the Chemicals Database, the same invention can be advantageously used to predict formulation outcomes for other varieties of dangerous or unlawful substances, such as chemical warfare agents, or narcotics or other illicit or unlicensed drugs, from inventories of potential source materials in a chemical cache, or even perform these additional evaluations at the same place and time, and on the same apparatus, as the HME formulation evaluation, analyzing a single set of observed materials for their association with these other products as well.

BRIEF DESCRIPTION OF THE DRAWINGS

FIG. 1 shows a block diagram outlining the steps of the instant method, including the optional use of an Inclusion List to check whether there is a need for further processing of a given Observed Material by determining whether it is included in any HME formulation of interest, and also including the optional performance-improving stratagem of performing the comparison between the chemical keys on the Observed Materials List and those listed under each HME in the HME Database, with the former listed in descending and the latter in ascending order, resulting in fewer wasted search steps.

FIG. 1(c) illustrates a specific embodiment of a HME Database for this invention, for an exemplary HME known as "APE."

FIG. 2 illustrates more fully the performance-enhancing method, shown in FIG. 1 and discussed above, of conducting a comparison between lists of unique keys representing materials on the Observed Materials List and those representing known source chemicals in HME formulations from the HME Database, by arranging in descending key order the OML list of source chemical keys before making the comparison to keys, arranged in ascending key order, in each HME formulation.

DETAILED DESCRIPTION OF THE INVENTION, INCLUDING DRAWINGS

Figure 1A:
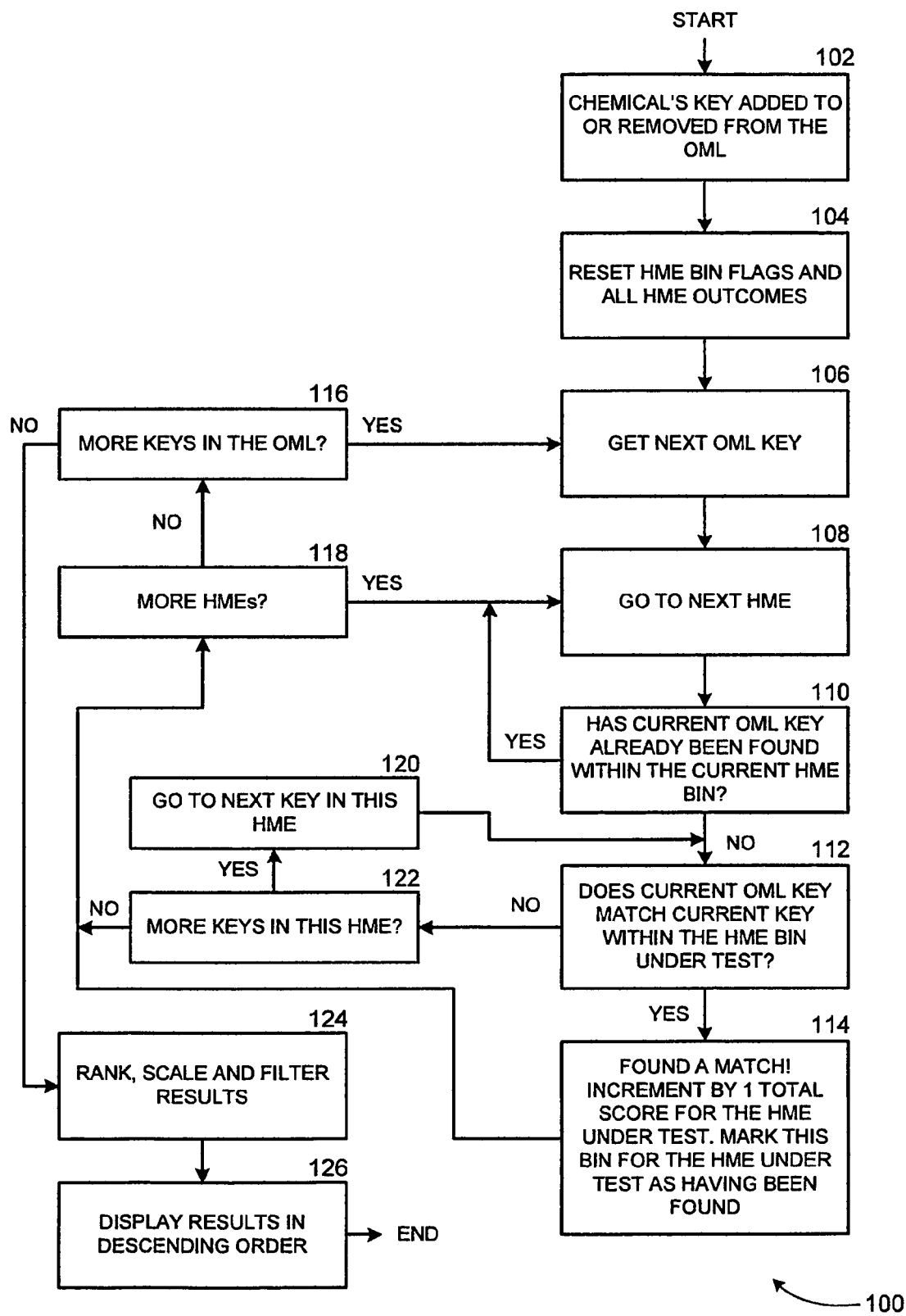
FIG. 1(a) shows a flow chart outlining the steps of the instant method in simplest form, in which none of the optional computer performance enhancing features have been incorporated.

The invention is described in more detail below:

The process requires providing a digital computer, with the required resources of processing devices, memory, and user input and output devices, that is programmed with machine instructions by which it carries out the following steps:

First, the computer must store in memory a Chemicals Database, a large reference database of chemicals, including source chemicals known to be used in the formulation of HMEs, with each listed source chemical represented by a unique key.

This Chemicals Database could conceivably comprise only the primary ingredients, or primary source chemicals, preferably used in directly formulating the explosives; however, in a highly advantageous embodiment the database also includes known secondary source chemicals, or alternative chemical ingredients that can, either as-is or with limited preliminary synthesis, be used to substitute for one or more primary ingredients in the manufacture of specific HMEs, again with each source chemical represented by a unique key. This proves useful, when, for example, the would-be explosives maker has found that the primary source chemicals are not readily available, or has concluded that the act of obtaining them, especially in large quantities, might itself arouse suspicion.

This, of course, results in a much larger Chemicals Database, including known primary and secondary source chemicals, and therefore potentially including many fairly ordinary chemicals which, again, may otherwise not have been suspected of potentially having application in the manufacture of HMEs.

In a highly advantageous embodiment, the Chemicals Database, available to users for choosing materials to be added to the Observed Materials List, also encompasses, in addition to the proper chemical name of each such source chemical, other terms by which each material might be identified by the user, including, where appropriate, trade name, CAS Registry® number assigned by the American Chemical Society, UN ID number assigned by the United Nations Committee of Experts on the Transport of Dangerous Goods, and RTECS (Registry of Toxic Effects of Chemical Substances) number, as well as phonetic spellings of chemical names and trade names, all associated with the same unique key as their respective chemical names. Selection of any such identifier from the Chemicals Database results in the addition of the selected chemical and its unique key to the Observed Materials List.

In another advantageous embodiment, the Chemicals Database is expanded to include additional chemicals of interest that may also be encountered at the search site or chemical cache being investigated. This permits the database to be used for purposes other than just predicting HME formulation outcomes. In one advantageous embodiment, the instant method is integrated in a single apparatus with methods for making other determinations with respect to the contents of the chemical cache, including whether some of those contents are themselves hazardous materials, and if so how to deal with them, quite aside from their possible status as HME precursors.

As noted earlier, in another advantageous embodiment, the same Chemicals Database can also encompass known precursors for other substances of concern, such as chemical warfare agents or illegal drugs. Used in conjunction with additional databases paralleling the HME Database for such substances, the method can, operating in the same manner, be used to predict formulation outcomes for those substances, based on the Observed Materials picked from an expanded Chemicals Database. In addition, because the HMEs themselves are dangerous chemicals, and may also be present in the chemical cache, with or without their source chemical precursors, in another advantageous embodiment, the Chemicals Database also encompasses many common HMEs themselves, both to allow their selection as Observed Materials for purposes of HME formulation outcomes (for those, like picric acid, that are both HMEs themselves and source chemicals for more complex HME formulations), and to permit their selection for purposes of another, optional program that can be installed on the same digital computer, that provides characteristics, blast radiuses, etc., for explosives found at the site.

Each listed chemical in the Chemicals Database is assigned a single, unique key, an identifier specific to that single chemical. That unique key for each chemical in the Chemicals Database could be any unique set of symbols, letters, alphanumeric characters or words, or numeric values, so long as each is associated with one, and only one, chemical in the Chemicals Database. In a particularly advantageous embodiment, that unique key associated with each listed chemical is an integer.

Second, the computer must also store in memory an HME Database, a database of materials used as source chemicals in the formulation of any of the HMEs of interest. Each such source chemical is assigned a unique key, identical to the one assigned to the same source chemical when it appears in the Chemicals Database. Again, to maximize its usefulness, the HME Database also incorporates both primary source chemicals and the secondary, alternative, source chemicals, if any, which can replace the preferred primary source materials, either by being directly substituted for the primary source materials in a primary chemical process producing the explosive, or by being transformed, in some preliminary reaction step, into a primary source chemical, which is then used in the primary chemical process for formulation of the HME sought to be produced.

In the HME Database, the known source chemicals for each HME formulation are grouped together, and, within an HME formulation, are grouped into separate "bins," with each bin containing the unique key representing a known primary source chemical required for that formulation, along with the unique keys representing all the secondary source chemicals that could be used in lieu of that primary source chemical, in that HME formulation.

Fourth, the computer is programmed to permit a user, utilizing the computer's user input device, to select from among the entries in the Chemicals Database, creating and storing in the computer memory a list, the Observed Materials List (OML), of materials to be analyzed. The computer places each such chemical (along with its unique key, though that key is itself not seen or selected by the user) on the OML. In one advantageous embodiment, the computer's user input device is a chemical sensor that automatically identifies the found chemical under evaluation, and transmits that identification directly to the digital computer, which then adds it, with its unique key, to the OML.

In a highly advantageous embodiment, a separate Inclusion List ("IL") is created and stored in the computer memory, comprising the unique keys of all source materials, primary and secondary, that are used in any of the HME formulations and therefore present in the HME Database, with each key listed only once. The following description of the comparison steps assumes the existence of such an Inclusion List, which allows a substantial performance improvement by avoiding the need to perform repeated searches for chemicals which aren't present in any HME formulation. However, the process can also be carried out without the use of such a list by simply skipping the step requiring checking a key representing a material on the Observed Materials List against the keys on the Inclusion List.

Fifth, the computer performs a comparison between each of the unique keys representing chemicals on the Observed Materials List (which also appear on the Inclusion List, if such an Inclusion List is being used), and the list of keys representing source chemicals in the HME Database, to determine which of the known HMEs have formulations that include at least one chemical placed on the Observed Materials List, and to calculate, using the algorithm described below, the relative likelihoods that the respective potential HMEs were those intended to be formulated from the observed source chemicals.

Ideally, the list of chemicals selected from the Chemicals Database for inclusion on the Observed Materials List would perfectly match one, and only one, explosive formulation identified in the HME Database. However, in the real world, some of the required source chemicals for a given formulation may not be found, even as secondary source materials; and some of the source chemicals found may have potential application to formulating more than one of the HMEs in the HME Database—potentially some having simple binary formulations, and some having more complex formulations, requiring additional source chemicals.

For example, if an explosive formulation uses picric acid as a necessary ingredient, the algorithm needs to account for the fact that a would-be explosive maker who was not able to obtain picric acid may nevertheless be able to use secondary ingredients to make picric acid, and then use that synthesized picric acid in the primary chemical process. As another example, the explosive TATP has as its necessary ingredients hydrogen peroxide, acetone, and sulfuric acid. Someone trying to formulate TATP may have difficulty obtaining high grade sulfuric acid, so may instead resort to using battery acid solution. Or, they may be unable to acquire high concentration hydrogen peroxide, and so may substitute the lower strength hydrogen peroxide that is commonly used in the beauty supply industry.

Thus, a critical part of the algorithm is that it must be able not only to rank the likelihood of the various possible formulations based on perfectly matching chemical components, but also to compensate by considering secondary chemicals that can, either in original form or given a bit of additional synthesis, be used as reasonable alternatives for critical primary HME ingredients. It must also handle situations where some necessary source materials are missing altogether, even when taking into account all known secondary source materials. Finally, it must differentiate, in evaluating likely HME outcomes, among multiple formulations, utilizing overlapping sets of source chemicals.

In its simplest form (FIG. 1(a)), chemicals on the observed materials list are compared with the HME formulations in the HME Database to determine the relative likelihoods that the observed materials were intended to be used to create specific HMEs, and the results are displayed for a user.

Figure 1B:
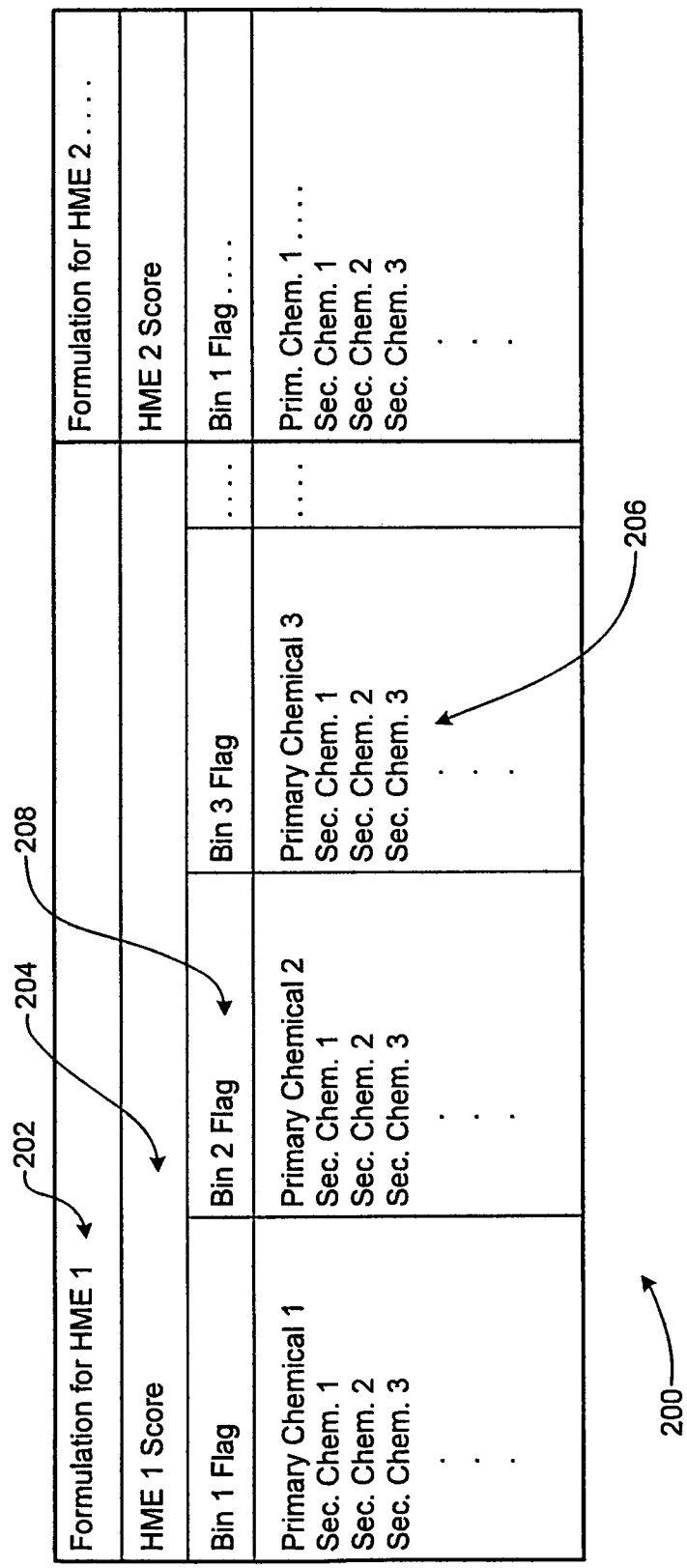
FIG. 1(b) shows an exemplary structure of a HME Database, showing the HME source materials organized by HME formulation, and each formulation organized by bins, each containing a primary and multiple secondary source materials for that HME formulation.

In a specific embodiment, the HME database is organized by HME (FIG. 1(b)). Each HME is in turn organized by a list of primary chemicals that are the components of each specific HME formulation. Each primary component is accompanied by a list of secondary/alternative chemicals that can be used in place of the primary component. The organization of the HME database shown in FIG. 1(b) is for illustrative purposes only, and the actual HME database can be organized in alternative ways inside the device.

FIG. 1(b) is a diagram illustrating a simplified organization of an HME database for the present invention. The HME database 200 includes HME formulations 202. Each HME formulation includes an HME score 204 and one or more bins 206, each listing one primary source chemical, and any number of secondary/alternative source chemicals that, together, make up the HME formulation. Each bin includes a bin flag 208. An actual implementation of an HME database may of course differ from that illustrated in FIG. 1(b), which is merely intended to show the elements of an HME database. In the real database, chemicals within a bin 206 will be represented by the unique chemical keys assigned in the Chemicals Database.

FIG. 1(*c*) is a diagram illustrating a specific embodiment of an HME database for the present invention. HME database 300 includes multiple HME formulations, of which a a typical formulation, 302, for the HME known as APE, is shown. Chemical keys 304 define possible components of APE, of which there are four required, represented by bins 0 through 3 (reference numeral 306). The primary source chemicals for each bin are indicated by the presence of a 1 (as at 308) in the right-hand column, opposite one of the 4 bin numbers. The chemical keys have been sorted into ascending numerical order to implement one performance-enhancing feature of the invention.

The comparison algorithm utilized by the computer, in one preferred embodiment, operates as follows, as illustrated by the flow chart presented as FIG. 1:

a. Starting with the first key representing a chemical placed in the OML, compare that OML key with the keys on the Inclusion List (IL) (again, assuming the use of such an Inclusion List as a performance enhancement—if an IL is not used, then, for each new OML key, this preliminary step of checking it against an IL is simply skipped. In another advantageous performance-enhancing embodiment, the OML keys are, for purposes of a later comparison step, sorted in descending order.)

b. If the OML key does not match any key on the Inclusion List, proceed directly to the next sequential OML key, c. If the OML key does match a key on the Inclusion List, compare that key sequentially, in key order, to the keys associated with each of the HME formulations within the HME Database, d. Each time a match is found between an OML key and a key representing either a primary source chemical, or any one or more of the secondary source chemicals, in a given HME bin (containing a primary source chemical and any number of secondary source chemicals), award its HME 1 point, flag that bin within that HME formulation as being found, indicating that no further comparisons are to be made between OML keys and any of the remaining HME keys within that bin, and proceed to compare the OML key with the keys in the unflagged bins in the remaining HME formulations in the HME Database.

e. Continue in like manner, comparing each new OML key first to the keys on the Inclusion List, if applicable, and then, if it matches a key on the IL, comparing it sequentially to the keys in unflagged bins in each HME formulation in the HME Database, and, for each HME bin in which a match between an OML key and an HME source chemical key is found, adding 1 point to the score of that HME, and flagging the bin as having contained a match to an OML chemical, so that HME bin will not be searched further for that OML key, or for any subsequent OML key.

Note that the process does not add additional points to an HME formulation for finding either both a primary and a secondary, or multiple secondary, source chemicals, in an HME bin (nor does it even search for such additional matches, once a single match is found in a given HME bin), so the maximum score for any HME is equal to the number of bins of primary and secondary source chemicals associated with that HME on the HME Database. Once a match is found between the Observed Materials List key and the key for a primary source chemical for an HME, the computer does not continue the search through the secondary source chemicals for that HME. Similarly, once a match is found between the Observed Materials List key and the key for any one secondary source material in an HME bin, the computer does not continue the search through the remaining secondary source chemicals in that HME bin. Once all the bins for an HME formulation that were not previously flagged as found have been checked against the OML key, the search continues sequentially through the remaining HME formulations, then, with the next OML key, sequentially through all the HME keys in unflagged HME bins, and so on until all materials on the Observed Materials List (that are also on the Inclusion List, if used) have been checked for matches to any of the HME formulations.

FIG. 1 shows a block diagram flow chart of the process, which incorporates the performance enhancements of using an Inclusion list, stopping searching further within an HME bin when any one match has been found to an OML key in that bin, flagging a bin in which a match is found so that it will not be subject to future searching, and inverting the keys in the OML so that, in searching HME formulations, the bottom of the list for an HME formulation moves up each time a match is found to a key under that formulation, or when the OML key is less than the current key within the HME under test.

f. When the comparison is complete, for each HME having at least one source chemical key from the HME Database that matches a key representing a chemical found on the Observed Materials List (i.e., at least one flagged bin), calculate that HME's percentage score—the point score of that HME divided by the total number of HME bins of source chemicals in that HME's formulation, multiplied by 100.

For example, the formulation for a simple binary explosive HME has just two bins, so if a match to an OML chemical is found in each of the two bins, that HME's score is 100%. If a different HME has four bins, each with one primary and any number of secondary source chemicals, and the comparison shows that the Observed Materials List includes matches to the primary source chemical in one bin, to at least one secondary source chemical each from two more of the bins, and to no source chemical from the fourth bin, its percentage score would be ((1+1+1 bins)/4 bins)×100%=75%.

An additional, optional, speed enhancement to the matching process can be achieved when, in a particularly advantageous embodiment illustrated in FIG. 2, the keys representing the Observed Materials List are arranged in descending order, and the list of keys in the HME Database are arranged in ascending order within each HME formulation, and the computer is programmed to start the search with the highest key on the Observed Materials List, and search each HME formulation in the HME Database, is where the keys for each HME are arranged in ascending order within that HME, for matches in descending order, against the OML's descending order list of keys. In this manner, since the keys match for the same chemical on each list, once the computer has completed searching the HME Database, matching the largest Observed Materials List key, and then ceasing searching the (now flagged) HME bin in which the match was found, each subsequent search for a match within an HME formulation to the next, always smaller, Observed Materials List key need proceed only as far down the HME key list for that HME as the key belonging to the last HME key for which a match was previously found, or the first HME key that is less than the OML key, whichever is encountered first, and then stop.

In FIG. 2, in searching for the first OML chemical, key 5, the computer starts at the first HME key in this formulation, on the right, at key 1. Iterating down toward the last HME key in this formulation, key 10, we find a match at key 5. This key 5 now becomes the bottom of the HME key list for this search, since, due to the inverted order of the lists, the next key on the OML cannot be any further down the HME list than key 5. Thus the bottom HME key to be searched moves up as the computer moves down through the list, in descending order of OML keys. This reduces the number of iterations required to search the HME key list for matches with the OML keys, saving computational steps.

This inverted-list searching method, combined with terminating the search for an Observed Materials List key as soon as it is found to be absent from the inclusion List, ceasing to search further within a bin once a match to an OML key has been found in that bin, and skipping searching any HME bin that has already been flagged as providing a match to any OML key, greatly speeds the search process, and allows it to be performed on a significantly less powerful digital computer, e.g., a palmtop computer, or even an enabled cellular telephone (though it can, of course, also be run on a more powerful desktop or laptop computer). As previously noted, FIG. 1 illustrates the operation of the search method with all of those performance enhancements in place—the blocks shown in dotted lines are those which represent these optional performance enhancing features. As noted above, FIG. 1(a) illustrates the search in simplest form, in which none of those computer performance enhancing features have been added.

g. Calculate a weighted percentage score, or relative likelihood, of the respective possible HME formulations (reflecting the reality that a would-be bomb maker would typically not, for example, have additional HME source chemicals present if the intent was only to make a very simple formulation like the binary explosive ANFO), by weighting each HME's percentage score by determining the HME with the largest total number of HME bins having keys matching an OML key, i.e., that with the largest point score, calculated as described above, and then normalizing the percentage scores as follows:

Weighted percentage score (relative likelihood) of each HME=(Percentage score of that HME)× ((Point score of that HME)/(Maximum point score achieved by any HME under evaluation)).

6. Rank the HMEs having any matches to the Observed Materials List by their resulting weighted percentage scores, or relative likelihoods, with that having the highest weighted percentage ranking number one, the second highest number two, and so on until all the HMEs having any source chemicals matched to chemicals on the Observed Materials List are accounted for, and list those HMEs in rank order.

7. Once the above analysis is completed, communicate the results, in terms of weighted percentages and relative ranking of the possible HME formulations, to the user via the provided user output device. This device would typically be a readable computer screen, though any method of communicating the results to the user could be substituted for, or used in addition to, such a screen readout.

Figure 3:
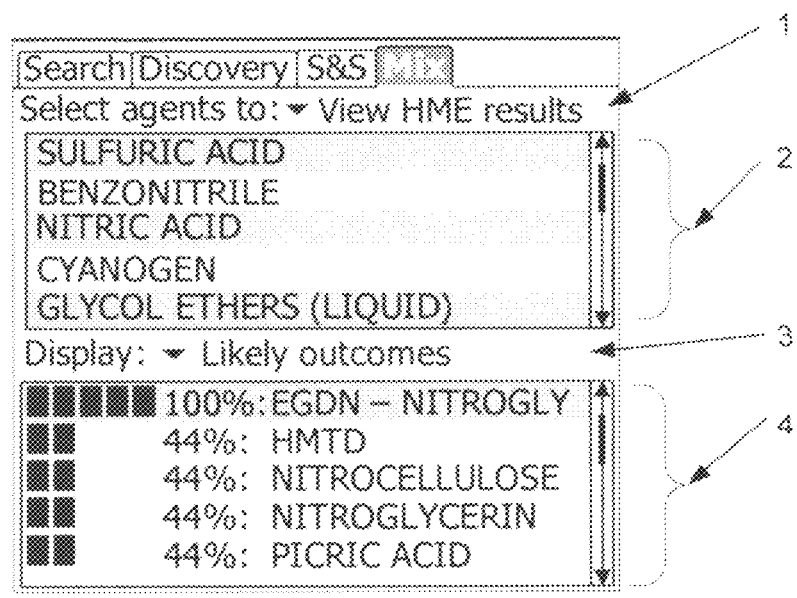
FIG. 3 shows a typical user output device screen, showing the HME formulation results of applying the instant method to a given sample set of Observed Materials.

The results can be reported in any convenient form. In one embodiment, the display would simply constitute a list of the HMEs found to have some matches, with their respective weighted percentage values, preferably in descending order of weighted percentage scores. In one advantageous embodiment, the display would take the form of a bar graph, visually highlighting the relative weighted percentage values for the respective HMEs as well as listing them, with the highest weighted percentage score at the top, with the longest bar, the second highest next, with the second longest bar, and so on. Also, while the display could simply show all HMEs having any matches at all with the Observed Materials List, in one advantageous embodiment the display would be limited to some preset number of the HMEs with the highest weighted percentage scores, in order to quickly focus the user on the most likely HME formulations. In another embodiment, the number of HMEs shown would, for the same reason, only include those whose weighted percentage scores exceeded some set value. FIG. 3 is a screen shot of a typical user output device screen, showing the results of applying the instant method to a sample set of Observed Materials, while running on a current generation smartphone. Here the OML chemicals are sulfuric acid, benzonitrile, nitric acid, cyanogens, and liquid glycol ethers. In the illustration, number 1 indicates that the user has selected to display HME formulation outcome results. Number 2 displays that the user has highlighted specific chemicals of interest, for inclusion on the Observed Materials List (OML). Number 3 indicates that the user has selected to view the probable outcomes, i.e., the most likely HME formulations corresponding to the OML inputs. Other options include viewing all possible HME formulations corresponding to these OML chemicals, or viewing a list of the key components of a given HME formulation. Number 4 displays the output of the algorithm that models which specific formulations are the most likely intended HMEs to be made from the selected set of chemicals. Here, the display shows the several most likely HME formulation outcomes corresponding to these source chemicals, which are picric acid, nitroglycerin, nitrocellulose, HMTD, and the most likely, with a weighted percentage score (relative likelihood) of 100%, is an explosive known as EGDN.

8. Repeat the preceding steps 3-7, first resetting all flags on HME bins, then re-searching for matches between OML keys and HME keys as described above, then recalculating the point scores, percentage scores, weighted percentage scores, and relative likelihood rankings, of the indicated HME formulations as described above, and immediately displaying the new results on the user output device, each time that a new chemical from the Chemicals Database is added to the Observed Materials List, or one of the previously entered OML entries is deleted.

This process of recalculating the point scores, percentage scores, weighted percentage scores, and likelihood rankings of HME formulations, and displaying the new results in "real time," permits the user to "home in on" suspected HME formulations, by selectively adding new items to the Observed Materials List, to more quickly confirm that a suspected HME is a likely formulation, or to perform "what if" tests to test the viability of various formulation hypotheses by adding or subtracting either real observed source chemical species, or hypothetical source chemicals that the user judges may clarify whether a particular suspected HME formulation is a likely outcome.

While the invention has been described in relation to the embodiments shown in the accompanying Drawing figures, other embodiments, alternatives, and modifications will be apparent to those skilled in the art. It is intended that the Specification be exemplary only, and that the true scope and spirit of the invention be indicated by the following claims.

I claim:

1. A system for predicting formulation outcomes for Substances of Concern (SOC) that correspond to a list of possible source chemicals, comprising:
   (a) a programmable platform including means for receiving a list of possible source chemicals and storing said list in a platform memory;
   (b) a SOC Formulations Database stored in a platform memory;

(c) programmable platform means for comparing the list of possible source chemicals with the SOC Formulations Database and for predicting the percentage score or relative likelihood of respective SOC formulation outcomes; and (d) programmable platform means for reporting said outcomes to a user.

2. A system for predicting chemical formulation outcomes for one or more Substances of Concern (SOC), comprising a digital computer, with required resources of processing devices, memory storage, and user input and output devices, and programmed with computer instructions, to carry out the following steps:

a. storing a SOC Formulations Database, containing source chemicals for various SOC formulations, with each chemical uniquely identified;

b. storing a Chemicals Database, in which chemicals that are also source chemicals in the SOC Formulations Database have the same identifiers as in the SOC Database;

c. receiving an Observed Materials List (OML), consisting of chemicals selected for analysis of their relationships to the SOC formulations;

d. comparing the OML chemicals to the source chemicals in the SOC formulations, calculating a percentage score or relative likelihood score for each SOC formulation based on the number of matches between that SOC's source chemicals and the OML chemicals; and e. displaying the scores or a graphical representation thereof of those SOC formulations on the user output device.

3. The system of claim 2, wherein each formulation in the SOC Formulations Database has its source chemicals divided into bins, with each bin containing one primary source chemical and any number of secondary source chemicals capable of being used, either directly or with limited preliminary synthesis, in lieu of that primary source chemical for that SOC, and wherein each SOC formulation receives a percentage score calculated on the basis of the number of bins in that formulation in which at least one primary or secondary source chemical matches an OML chemical.

4. The system of claim 3, wherein, after calculating the percentage scores of the various SOC formulations having at least one match to the OML chemicals, the system also calculates a weighted percentage score for each such SOC formulation by normalizing that SOC's percentage score against that of the SOC formulation with the highest point score, producing a relative likelihood of each SOC formulation corresponding to the OML chemicals, then ranks those SOC formulations in order of their relative likelihoods, and displays the weighted percentage scores and rankings of those formulations, or a graphical representation thereof, on the user output device.

5. The system of claim 4, wherein, each time that a chemical is either added to or deleted from the Observed Materials List, the scores, relative likelihoods, and rankings of the identified SOC formulations are automatically recalculated, and the new results displayed on the user output device.

6. The system of claim 2, wherein, after calculating the respective scores of the various SOC formulations having matches to the OML chemicals, the system also ranks those formulations in order of their scores, and displays the scores and rankings of those formulations, or a graphical representation thereof, on the user output device.

7. The system of claim 2, wherein chemicals are placed on the OML by a user entering them via the user input device.

8. The system of claim 2, wherein chemicals are placed on the OML by a user selecting them from the Chemicals Database via the user input device.

9. The system of claim 8, wherein the Chemicals Database also contains, associated with each uniquely identified chemical, additional or alternative names and identifiers by which that chemical is commonly known, including, where each exists, its trade names, CAS Registry® number, UN ID number, RTECS number, and phonetic spellings of both chemical names and trade names, such that a user's selection of any such alternative name or identifier from the Chemicals Database results in the addition of the corresponding uniquely identified chemical to the Observed Materials List.

10. The system of claim 8, wherein the Chemicals Database also incorporates hazardous materials and other Substances of Concern (SOC), to permit their selection from the Chemicals Database for purposes of carrying out other processes programmed on the same digital computer, assessing the significance of the presence of said hazardous materials and SOCs themselves, independent of whether such materials are also source materials for any SOC formulations.

11. The system of claim 2, wherein the user input device is a chemical sensor, which analyzes and identifies a sample of a chemical, and inserts the chemical's identification directly into the Observed Materials List.

12. The system of claim 2, wherein the Chemicals Database contains primary and secondary source chemicals from the SOC Formulation Database.

13. The system of claim 2, wherein, each time that a chemical is either added to or deleted from the Observed Materials List, the scores of the identified SOC formulations are automatically recalculated, and the new results displayed on the user output device.

14. The system of claim 2, wherein the Substances of Concern (SOC) consist of one or more formulations of substances of concern, including but not limited to Home Made Explosives (HME), Chemical Warfare Agents (CW), and Illicit Drugs (ID).

15. The system of claim 2, wherein the Substances of Concern (SOC) consist of one or more formulations of Home Made Explosives (HME), Chemical Warfare Agents (CW), and Illicit Drugs (ID).

16. The system of claim 2, wherein the provided user output device comprises a display on which the output is in the form of a graphical representation, visually highlighting the relative scores for any SOCs found to have matches to any OML chemicals.

17. The system of claim 2, in which the digital computer, with required resources of processing devices, memory storage, and user input and output devices, and programmed with computer instructions for performing the specified steps, takes the form of a handheld computational device.

18. The system of claim 2, wherein each formulation in the SOC Formulations Database has its source chemicals divided into bins, with each bin containing one primary source chemical and any number of secondary source chemicals capable of being used, either directly or with limited preliminary synthesis, in lieu of that primary source chemical for that SOC, and wherein each SOC formulation receives a percentage score calculated on the basis of the number of bins in that formulation in which at least one primary or secondary source chemical matches an OML chemical; and wherein chemicals can be placed on the OML in one or more of the following ways:

by a user entering them via the user input device, by a user selecting them from the Chemicals Database via the user input device, by a user utilizing a user input device which is a chemical sensor, and which analyzes and identifies a sample of a chemical and inserts the chemical's identification directly into the Observed Materials List; and wherein, after calculating the percentage scores of the various SOC formulations having at least one match to the OML chemicals, the system also calculates a weighted percentage score for each such SOC formulation by normalizing that SOC's percentage score against that of the SOC formulation with the highest point score, producing a relative likelihood of each SOC formulation corresponding to the OML chemicals, then ranks those SOC formulations in order of their relative likelihoods, and displays the weighted percentage scores and rankings of those formulations, or a graphical representation thereof, on the user output device; and wherein, each time that a chemical is either added to or deleted from the Observed Materials List, the scores, relative likelihoods, and rankings of the identified SOC formulations are automatically recalculated, and the new results displayed on the user output device.

19. The system of claim 18, wherein the Chemicals Database also contains, associated with each uniquely identified chemical, additional or alternative names and identifiers by which that chemical is commonly known, including, where each exists, its trade names, CAS Registry® number, UN ID number, RTECS number, and phonetic spellings of both chemical names and trade names, such that a user's selection of any such additional or alternative name or identifier from the Chemicals Database results in the addition of the corresponding uniquely identified chemical to the Observed Materials List; and wherein the digital computer, with required resources of processing devices, memory storage, and user input and output devices, and programmed with computer instructions for performing the specified steps, takes the form of a handheld computational device.

20. A method for predicting formulation outcomes for Substances of Concern (SOC) that correspond to a list of possible source chemicals, comprising using:
(a) a programmable platform including means for receiving a list of possible source chemicals and storing said list in a platform memory;
(b) a SOC Formulations Database stored in a platform memory;
(c) programmable platform means for comparing the list of possible source chemicals with the SOC Formulations Database and for predicting the percentage score or relative likelihood of respective SOC formulation outcomes; and
(d) programmable platform means for reporting said outcomes to a user.

21. A method for predicting chemical formulation outcomes for one or more Substances of Concern (SOC), comprising providing a digital computer, with required resources of processing devices, memory storage, and user input and output devices, and programmed with computer instructions, and having the computer carry out the following steps:
a. storing a SOC Formulations Database, containing source chemicals for various SOC formulations, with each chemical uniquely identified;
b. storing a Chemicals Database, in which chemicals that are also source chemicals in the SOC Formulations Database have the same identifiers as in the SOC Database;

c. receiving an Observed Materials List (OML), consisting of chemicals selected for analysis of their relationships to the SOC formulations;
d. comparing the OML chemicals to the source chemicals in the SOC formulations, calculating a percentage score or relative likelihood score for each SOC formulation based on the number of matches between that SOC's source chemicals and the OML chemicals, and
e. displaying the scores of those SOC formulations, or a graphical representation thereof, on the user output device.

22. The method of claim 21, wherein each formulation in the SOC Formulations Database has its source chemicals divided into bins, with each bin containing one primary source chemical and any number of secondary source chemicals capable of being used, either directly or with limited preliminary synthesis, in lieu of that primary source chemical for that SOC, and wherein each SOC formulation receives a percentage score calculated on the basis of the number of bins in that formulation in which at least one primary or secondary source chemical matches an OML chemical.

23. The method of claim 22, wherein, after calculating the percentage scores of the various SOC formulations having at least one match to the OML chemicals, the system also calculates a weighted percentage score for each such SOC formulation by normalizing that SOC's percentage score against that of the SOC formulation with the highest point score, producing a relative likelihood of each SOC formulation corresponding to the OML chemicals, then ranks those SOC formulations in order of their relative likelihoods, and displays the weighted percentage scores and rankings of those formulations, or a graphical representation thereof, on the user output device.

24. The method of claim 23, wherein, each time that a chemical is either added to or deleted from the Observed Materials List, the scores, relative likelihoods, and rankings of the identified SOC formulations are automatically recalculated, and the new results displayed on the user output device.

25. The method of claim 21, wherein, after calculating the respective scores of the various SOC formulations having matches to the OML chemicals, the system also ranks those formulations in order of their scores, and displays the scores and rankings of those formulations, or a graphical representation thereof, on the user output device.

26. The method of claim 21, wherein chemicals are placed on the OML by a user entering them via the user input device.

27. The method of claim 21, wherein chemicals are placed on the OML by a user selecting them from the Chemicals Database via the user input device.

28. The method of claim 21, wherein the user input device is a chemical sensor, which analyzes and identifies a sample of a chemical, and inserts the chemical's identification directly into the Observed Materials List.

29. The method of claim 21, wherein the Chemicals Database also contains, associated with each uniquely identified chemical, additional or alternative names and identifiers by which that chemical is commonly known, including, where each exists, its trade names, CAS Registry® number, UN ID number, RTECS number, and phonetic spellings of both chemical names and trade names, such that a user's selection of any such additional or alternative name or identifier from the Chemicals Database results in the addition of the corresponding uniquely identified chemical to the Observed Materials List.

30. The method of claim 21, wherein the Chemicals Database also incorporates hazardous materials and other Substances of Interest (SOC), to permit their selection from the Chemicals Database for purposes of carrying out other processes programmed on the same digital computer, assessing the significance of the presence of said hazardous materials and SOCs themselves, independent of whether such materials are also source materials for any SOC formulations.

31. The method of claim 21, wherein each formulation in the SOC Formulations Database has its source chemicals divided into bins, with each bin containing one primary source chemical and any number of secondary source chemicals capable of being used, either directly or with limited preliminary synthesis, in lieu of that primary source chemical for that SOC, and wherein each SOC formulation receives a percentage score calculated on the basis of the number of bins in that formulation in which at least one primary or secondary source chemical matches an OML chemical; and wherein chemicals can be placed on the OML in one or more of the following ways:
by a user entering them via the user input device,
by a user selecting them from the Chemicals Database via the user input device,
by a user utilizing a user input device which is a chemical sensor, and which analyzes and identifies a sample of a chemical and inserts the chemical's identification directly into the Observed Materials List; and wherein, after calculating the percentage scores of the various SOC formulations having at least one match to the OML chemicals, the system also calculates a weighted percentage score for each such SOC formulation by normalizing that SOC's percentage score against that of the SOC formulation with the highest point score, producing a relative likelihood of each SOC formulation corresponding to the OML chemicals, then ranks those SOC formulations in order of their relative likelihoods, and displays the weighted percentage scores and rankings of those formulations, or a graphical representation thereof, on the user output device; and wherein, each time that a chemical is either added to or deleted from the Observed Materials List, the scores, relative likelihoods, and rankings of the identified SOC formulations are automatically recalculated, and the new results displayed on the user output device.

32. The method of claim 31, wherein the Chemicals Database also contains, associated with each uniquely identified chemical, additional or alternative names and identifiers by which that chemical is commonly known, including, where each exists, its trade names, CAS Registry® number, UN ID number, RTECS number, and phonetic spellings of both chemical names and trade names, such that a user's selection of any such additional or alternative name or identifier from the Chemicals Database results in the addition of the corresponding uniquely identified chemical to the Observed Materials List; and wherein the digital computer, with required resources of processing devices, memory storage, and user input and output devices, and programmed with computer instructions for performing the specified steps, takes the form of a handheld computational device.

33. A computer program product, stored on non-transitory machine-readable media, the program comprising machine executable instructions for predicting chemical formulation outcomes for one or more Substances of Concern (SOC), that correspond to a list of possible source chemicals, by carrying out, on a digital computer, with required resources of processing devices, memory storage, and user input and output devices, and programmed with computer instructions, the steps of:

a. storing a SOC Formulations Database, containing source chemicals for various SOC formulations, with each chemical uniquely identified;
b. storing a Chemicals Database, in which chemicals that are also source chemicals in the SOC Formulations Database have the same identifiers as in the SOC Database;
c. receiving an Observed Materials List (OML), consisting of chemicals selected for analysis of their relationships to the SOC formulations;
d. comparing the OML chemicals to the source chemicals in the SOC formulations, calculating a percentage score or relative likelihood for each SOC formulation based on the number of matches between that SOC's source chemicals and the OML chemicals, and
e. displaying the scores of those SOC formulations, or a graphical representation thereof, on the user output device.

* * * * *

UNITED STATES PATENT AND TRADEMARK OFFICE
CERTIFICATE OF CORRECTION

| | |
|---|---|
| PATENT NO. | : 9,087,300 B2 |
| APPLICATION NO. | : 13/507402 |
| DATED | : July 21, 2015 |
| INVENTOR(S) | : Gregory Albert Ouzounian |

Page 1 of 1

It is certified that error appears in the above-identified patent and that said Letters Patent is hereby corrected as shown below:

In the claims

At column 12, line 4, claim 9 depends from the system of claim 2, rather than of claim 8.

At column 12, line 14, claim 10 depends from the system of claim 2, rather than of claim 8.

Signed and Sealed this
First Day of March, 2016

Michelle K. Lee
*Director of the United States Patent and Trademark Office*